United States Patent
Comelli et al.

(10) Patent No.: US 6,548,550 B1
(45) Date of Patent: Apr. 15, 2003

(54) PHARMACEUTICAL COMPOSITIONS CONTAINING N-PALMITOYLETHANOLAMIDE AND USE THEREOF IN THE VETERINARY FIELD

(75) Inventors: Cristina Comelli, Padova (IT); Maria Federica Della Valle, Padova (IT); Francesco Della Valle, Padova (IT); Gabriele Marcolongo, Due Carrare (IT)

(73) Assignee: Innovet Italia S.r.l., Milan (IT)

( * ) Notice: Subject to any disclaimer, the term of this patent is extended or adjusted under 35 U.S.C. 154(b) by 0 days.

(21) Appl. No.: 10/030,060

(22) PCT Filed: Aug. 6, 1999

(86) PCT No.: PCT/IT99/00259

§ 371 (c)(1),
(2), (4) Date: Jan. 4, 2002

(87) PCT Pub. No.: WO01/10434

PCT Pub. Date: Feb. 15, 2001

(51) Int. Cl.$^7$ .................................................. A61K 31/16
(52) U.S. Cl. ........................................................ 514/625
(58) Field of Search .......................................... 514/625

(56) References Cited

FOREIGN PATENT DOCUMENTS

EP    550 006 A2  * 12/1991
EP    550 008 A2  *  7/1993

OTHER PUBLICATIONS

Mazzari S, et al, Eu. J. Pharmacology, 300, 1996, 227–236.*

* cited by examiner

*Primary Examiner*—Rebecca Cook
(74) *Attorney, Agent, or Firm*—Kalow & Springut LLP

(57) ABSTRACT

The present invention relates to a method for treating eosinophilic granuloma in a Feline comprising administering a pharmaceutical composition, the composition comprising N-palmitoylethanolamide. The present invention also relates to said pharmaceutical composition and the process for the preparation thereof.

8 Claims, No Drawings

PHARMACEUTICAL COMPOSITIONS CONTAINING N-PALMITOYLETHANOLAMIDE AND USE THEREOF IN THE VETERINARY FIELD

This is a 371 of PCT/IT99/00259 filed Aug. 6, 1999.

The present invention relates to pharmaceutical compositions containing N-palmitoylethanolamide (palmidrol) for use in the veterinary field, particularly for the treatment of the eosinophilic skin condition in felines which is normally known as Eosinophilic Granuloma Complex, and of tendonous keloids in horses.

The eosinophilic condition in felines (Moriello K et al, 1997, Handbook of Small Animal Dermatology, pp. 205–208, Pergamon Press) has clinical signs such as erythema, pruritis and alopecia, and skin symptoms which are recognizable in the form of eosinophilic plaque (EP), eosinophilic granuloma (EG), and miliary or papulo-scabby dermatitis, which can appear in the animal individually or simultaneously or at different times.

EP is a circumscribed area of erosion and exudation associated with clinical signs such as erythema, pruritis and auto-induced alopecia. Although they may appear anywhere on the skin surface, the lesions are located preferentially in the inguinal or perianal regions or in the medial region of the upper rear leg. The characteristic hystopathology of EP shows considerable cell infiltration in the perivascular spaces, associated with epidermal hyperplasia, spongiosis and ulceration.

EG appears as an erythematous, alopecic and raised area generally located on the caudal face of the rear paws on the extremities (the claw bed and the pads), in the oral cavity, or on the chin. The characteristic hystopathology of EG appears as a diffuse granulomatous dermatitis associated with areas of collagenolysis.

Miliary dermatitis is similar to EP but less extensive and with the formation of scabs.

Regardless of whether it is in the form of EP or EG, eosinophilic granuloma with lesions, is a highly recurrent condition. For this reason, animals suffering from eosinophilic granuloma, in the form either of EP or of EG, are subject throughout their lives, to intermittent or continuous treatments with antihistamines and corticosteroids the side effects of which, particularly in treatment of long duration, are known and documented.

The identification of active ingredients which can alleviate or resolve the inflammatory picture, at the same time ensuring maximum tolerability and an absence of adverse reactions, is an objective of considerable interest in veterinary treatment.

Tendonous keloids represent one of the most common chronic manifestations of tendinitis which arise in horses—and in particular in competition horses—as a result of acute inflammations of the tendons, as well as partial or complete traumatic lesions and also lesions associated with haemorrhage and oedema.

Tendonous keloids appear as soft, easily palpable masses of variable sizes and are constituted by fibrous tissue with thickenings and adhesions in the peritendonous area. Horses with chronic tendon symptoms of this type notice pain with clear lameness which greatly comprise their competitive performance.

The treatment of these symptoms, when they are chronic, is particularly complex since the anti-inflammatory drugs normally used (FANS and corticosteroids) are more effective in the acute phases than in the consequent chronic manifestations.

Up to now, various treatments have been tried with little success; in particular, it has been noted that the intratendonous administration of corticosteroids is contraindicated. Up to now, use has been made of very questionable operations such as superficial burning, percutaneous splitting of the tendons, or implantation of carbon fibres.

Basically, up to the present time, there has been no pharmacological treatment which has solved the chronic symptomatic manifestations of tendinitis in horses.

It has now surprisingly been found that N-palmitoylethanolamide (common international name palmidrol) is effective in the treatment of eosinophilic granuloma in cats, for both EP and EG lesions, and of tendonous keloids in horses. In the latter case in particular, a complete recovery of the animal with the possibility of a return to the competition circuit has been confirmed.

The subject of the present invention is therefore the use of n-palmitoylethanolamide, preferably in micronized and/or co-micronized form, for the preparation of pharmaceutical compositions for veterinary use, particularly for the treatment of eosinophilic granuloma in cats, for both EP and EG lesions, and of tendonous keloids in horses.

A further subject of the present invention is pharmaceutical compositions containing N-palmitoylethanolamide in micronized and/or co-micronized form.

The treatment of cats with N-palmitoylethanolamide provides for the administration of the drug in quantities of from 1 to 50 mg/kg/die for a period of between 15 and 60 days. A preferred treatment scheme provides for a daily administration of 10 mg/kg of body weight for 30 consecutive days.

The treatment of horses with N-palmitoylethanolamide provides for the administration of the drug in quantities of from 0.5 to 5 g/die, preferably 2 g/die for a period of between 20 and 150 consecutive days, preferably between 30 and 120 days.

The following examples explain the invention and the preferred method of implementing it without, however, being limiting thereof.

BIOLOGICAL EXAMPLES

Example A

Effect of Oral Treatment with N-palmicoylethanolamide in Eosinophilic Skin Condition in Cats Method Included in the investigation were 15 cats of European race with short hair, of which 9 were female and 6 were male, with ages of between 7 and 123 months. All of the animals had symptoms of the eosinophilic condition, such as pruritis, alopecia and erythema, and the skin manifestations associated therewith and, more precisely, 6 subjects had EP, 5 had EG and 4 had milary dermatitis (scabs). A numerical evaluation relating to the intensity and location of the signs and symptoms was assigned to each individual animal in accordance with the P.A.S.I. (psoriasis area severity index) "score" (Marks R. et al., 1989, Arch. Dermatol., 125:235–240). The improvements in the clinical signs and in the associated lesions were evaluated on the 15th and 30th days of treatment. The treatment consisted of a preparation in accordance with Example 3 of the pharmaceutical preparations given below, containing 120 mg of micronized N-palmitoylethanolamide. The active ingredient was administered in a proportion of 10 mg/kg/die for 30 days.

Table 1 below summarizes the results of the test (PEA= N-palmitoylethanolamide):

| | SYMPTOMS pruritis-erythema-alopecia % | | | SIGNS plaque-granuloma-miliary scabs % | | |
|---|---|---|---|---|---|---|
| | im-proved | un-changed | worsened | im-proved | un-changed | worsened |
| not treated | | | | | | |
| T15 | 0 | 80 | 20 | 0 | 85 | 15 |
| T30 | 0 | 70 | 30 | 0 | 80 | 20 |
| treated with composition of Example 3 | | | | | | |
| T15 | 14.3 | 85.7 | 0 | 30 | 70 | 0 |
| T30 | 67 | 33 | 0 | 66.7 | 33.3 | 0 |
| treated with non-micronized PEA (10 mg/kg/die) | | | | | | |
| T15 | 8.2 | 91.8 | 0 | 14.6 | 85.4 | 0 |
| T30 | 52 | 48 | 0 | 51.4 | 48.6 | 0 |
| treated with cortisones | | | | | | |
| T15 | 28 | 72 | 0 | 40 | 60 | 0 |
| T30 | 65 | 35 | 0 | 64.8 | 35.2 | 0 |

Example B

Effect of Oral Treatment with N-palmitoylethanolamide in the Treatment of Tendonous Keloids in Competition Horses Case 1

On initial examination, an 8 year-old thoroughbred male chestnut racehorse had a large keloid, soft to the touch, in the palmar region of the metacarpal of the lower left-hand limb in a proximal position on the profound flexor tendon. The horse had undergone an operation on the above-mentioned tendon 6 months previously for serious traumatic lesion of the sheath. The animal had a pronounced limp and was practically immobilized.

Treatment for 30 days with the preparation of Example 1 of the pharmaceutical compositions given below, involving administration of 2 g/die of micronized N-palmitoylethanolamide, brought about a regression of the keloid by between 90 and 95%.

The animal was able to recommence competitive activity.

Case 2

Upon examination, a 3-year-old half-breed female bay racehorse had a spheroidal formation the size of a lemon, of soft connective tissue in the latero-palmar region of the metacarpal of the left-hand front limb. The keloidal formation was connected to the profound flexor tendon. The tendon had been burnt about four months previously. After treatment for 30 days with the preparation of Example 1 of the pharmaceutical preparations given below, involving the administration of 2 g/die of micronized N-palmitoylethanolamide, the formation regressed completely and the functionality of the tendon was completely restored.

Case 3

A 5-year-old male bay racehorse, had signs of recurrent, chronic tendon inflammation on the right-hand front profound flexor. 2 years previously, the subject had undergone a tendonectomy for lesion to the sheath, from which it had never fully recovered. After treatment for 30 days with the preparation of Example 1 of the pharmaceutical preparations given below, involving the administration of 2 g/die of micronized N-palmitoylethanolamide, the tendon was clearly reduced. After a further 30 days with the same treatment regime, the subject was completely cured with considerable benefit to its competitive performance.

Case 4

A 2 year-old thoroughbred male bay racehorse had acute tendinitis of the right-hand front profound flexor in the full inflammatory phase. As a result of an operation performed for the reduction of tendonous oedema, the animal developed a considerable fibrotic reaction with the production of adhesions. 5 months after the operation, treatment was started with the preparation of Example 1 of the pharmaceutical Preparations given below, involving the administration of 2 g/die of micronized N-palmitoylethanolamide. After 30 days a considerable improvement was noted and the treatment was continued for a further 60 days.

After treatment for 90 days, the tendon was perfectly shaped and the adhesions previously found had completely regressed. The animal returned to competitive activity.

It is clear from the results given above that N-palmitoylethanolamide can advantageously be used in the treatment of eosinophilic granuloma in cats, for both EP and EG lesions, and of tendonous keloids in horses, both when these conditions are acute and when they are chronic.

In the latter animal in particular, the treatment with N-palmitoylethanolamide seems to be the only effective cure for tendonous keloids which enables the horse to return to competitive activity.

The treatment of the cat with N-palmitoylethanolamide, on the other hand, gave results comparable to treatment with cortisones, with the substantial advantage that it does not have the serious side effects typical of these drugs.

The use of N-palmitoylethanolamide in micronized and/or co-micronized form (for example, with lactose) is particularly advantageous in bringing about the positive outcome of the treatment.

Clearly, the use of N-palmitoylethanolamide, preferably in micronized and/or co-micronized form, for the treatment of eosinophilic granuloma in cats, for lesions in both EP and EG forms, and of tendonous kelids in horses, may be extended to all animals, particularly felines and equines, which have conditions of the same type.

PREPARATION OF N-PALMITOYLETHANOLAMIDE (PEA)

PEA is a known compound and can be prepared in accordance with the synthesis method described in EP 0 550 008 which is incorporated herein by reference.

The micronization of PEA and its co-micronization with excipients were performed with compressed-air turbine micronizing apparatus. This apparatus is known and is not therefore described in greater detail.

The product obtained was subjected to analysis of the particles with Mastersizer, $\mu$ version apparatus from Malvern Instruments Co. UK. The final fineness of the PEA particles produced can be summarized as follows:

| particle size | quantity % |
|---|---|
| >14μ | traces |
| <10μ | 96% approx. |
| <6μ | 80% |

It should be noted that this result of the micronization method obtained with PEA is surprising since it is unusual for a molecule of a lipid nature to produce particles with a mean fineness much less than 10μ. The extreme fineness of the particles can be translated into improved absorption of the drug.

EXAMPLES OF PHARMACEUTICAL PREPARATIONS

Example 1

Oral Powder for Horses

| 100 g contained: | |
|---|---|
| micronized N-palmitoylethanolamide | 22.22 g |
| maize starch | 77.78 g |

Example 2

Oral Granules for Horses

| 100 g contained: | |
|---|---|
| N-palmitoylethanolamide co-micronized with lactose | 35.0 g |
| lactose co-micronized with N-palmitoyl-ethanolamide | 28.0 g |
| maize starch | 27.0 g |
| carboxymethyl cellulose | 10.0 g |

Example 3

Tablets for Cats

| Each tablet, divisible from 350 g, contained: | |
|---|---|
| micronized N-palmitoylethanolamide | 120 mg |
| maize starch | 30 mg |
| lactose | 115 mg |
| carboxymethyl cellulose | 15 mg |
| microcrystalline cellulose | 60 mg |
| magnesium stearate | 10 mg |

Example 4

Oily Gel for Cats

| 100 g contained: | |
|---|---|
| N-palmitoylethanolamide co-micronized with lactose | 2.5 g |
| lactose co-micronized with N-palmitoylethanolamide | 1.5 g |
| soya lecithin | 82.5 g |
| geleol | 12.0 g |
| Vitamin E acetate | 0.5 g |

Example 5

Gel for Use on Oral Mucosae in Cats

| 100 g contained: | |
|---|---|
| micronized N-palmitoylethanolamide | 300 mg |
| hyaluronic acid, sodium salt (titrated in bio-binding epitope) | 200 mg |
| carbomer | 280 mg |
| methyl paraoxybenzoate | 200 mg |
| ethyl paraoxybenzoate | 50 mg |
| fish flavouring | 800 mg |
| sorbitol | 20 g |
| demineralized water to make up to | 100 g |

In general, a composition for administration to cats contains from 20 mg to 4 g of PEA per 100 g of composition. A composition for administration to horses contains from 15 g to 40 g of PEA per 100 g of composition.

Clearly, other pharmaceutical compositions containing a pharmacologically effective dose of N-palmitoylethanolamide together with pharmacologically acceptable excipients may be provided. These compositions may be in the form of capsules, tablets, powders and pellets, and also in gastroresistant formulations for oral administration and may also be produced with the use of preliminary microencapsulation, liposomization or micellization techniques. For topical routes, including the transdermal route, formulations in suppositories, micro-enemas, creams, ointments, sprays, gels, foams, dressings of various thicknesses and patches may be used. All possible pharmaceutical forms indicated for the various administration routes may also be formulated with excipients or by technological processes suitable for producing fast-release or slow-release medicaments.

What is claimed is:

1. A method for treating eosinophilic granuloma in a Feline, said method comprising administering a pharmaceutical composition, wherein the composition is comprised of N-palmitoylethanolamide.

2. The method according to claim 1, wherein the Feline is a cat.

3. The method according to claim 1, wherein the N-palmitoylethanolamide is present in micronized form or is co-micronized with an excipient.

4. A pharmaceutical composition comprised of N-palmitoylethanolamide in micronized form or co-micronized with an excipient, together with pharmaceutically acceptable excipients.

5. The pharmaceutical composition according to claim 4 comprising from 20 mg to 4 g of N-palmitoylethanolamide per 100 g of composition.

6. The pharmaceutical composition according to claim 4 comprising from 15 g to 40 g of N-palmitoylethanolamide per 100 g of composition.

7. The pharmaceutical composition according to claim 4 in a form chosen from the group consisting of oral powder, oral granules, tablets and gel.

8. A process for the preparation of a pharmaceutical composition comprising the step of micronizing or co-micronizing N-palmitoylethanolamide with an excipient.

* * * * *